(12) United States Patent
Hemond et al.

(10) Patent No.: US 8,740,838 B2
(45) Date of Patent: Jun. 3, 2014

(54) INJECTION METHODS USING A SERVO-CONTROLLED NEEDLE-FREE INJECTOR

(75) Inventors: Brian D. Hemond, Lexington, MA (US); Ian W. Hunter, Lincoln, MA (US); Andrew J. Taberner, Auckland (NZ); Dawn M. Wendell, Farmington, CT (US); N. Catherine Hogan, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 131 days.

(21) Appl. No.: 13/269,421

(22) Filed: Oct. 7, 2011

(65) Prior Publication Data

US 2012/0089114 A1 Apr. 12, 2012

Related U.S. Application Data

(60) Provisional application No. 61/391,045, filed on Oct. 7, 2010.

(51) Int. Cl.
*A61M 5/30* (2006.01)

(52) U.S. Cl.
USPC .................. 604/68; 604/65; 604/66; 604/70; 604/503

(58) Field of Classification Search
USPC .................................. 604/57–64, 68–72, 503
See application file for complete search history.

(56) References Cited

U.S. PATENT DOCUMENTS

| 5,879,327 | A | 3/1999 | Moreau DeFarges et al. |
| 6,673,033 | B1 * | 1/2004 | Sciulli et al. ..................... 604/67 |
| 6,939,323 | B2 | 9/2005 | Angel et al. |
| 7,066,922 | B2 | 6/2006 | Angel et al. |

(Continued)

FOREIGN PATENT DOCUMENTS

| WO | WO-03/035149 A1 | 5/2003 |
| WO | WO-03/037403 A1 | 5/2003 |

(Continued)

OTHER PUBLICATIONS

Hemond, Brian D., et al., "A Lorentz-Force Actuated Autoloading Neddle-free Injector," Proceedings of the 28th IEEE, EMBS Annual International Conference, Aug. 30-Sep. 3, 2006, pp. 679-682.

(Continued)

*Primary Examiner* — Emily Schmidt
(74) *Attorney, Agent, or Firm* — Hamilton Brook Smith & Reynolds, P.C.

(57) ABSTRACT

A method for injecting a substance through a biological body surface includes providing a needle-free transdermal transport device configured to inject the substance through the surface. The substance is injected into the biological body with the transport device while a parameter of the injection is sensed and a servo-controller is used to dynamically adjust at least one injection characteristic based on the sensed parameter. The substance is injected for (i) a first time period during which a first portion of a volume of the substance is injected at a first injection pressure, and (ii) a second time period during which a remainder of the volume of the substance is injected at a second injection pressure. A viscosity of the substance may be determined, and a pressure calculated for injecting the substance based on the viscosity. The substance may be injected with the transport device by using the calculated pressure.

15 Claims, 12 Drawing Sheets

(56) References Cited

U.S. PATENT DOCUMENTS

| | | | |
|---|---|---|---|
| 7,364,568 | B2 | 4/2008 | Angel et al. |
| 7,425,204 | B2 | 9/2008 | Angel et al. |
| 7,429,258 | B2 | 9/2008 | Angel et al. |
| 7,530,975 | B2 | 5/2009 | Hunter |
| 7,645,263 | B2 | 1/2010 | Angel et al. |
| 7,651,475 | B2 | 1/2010 | Angel et al. |
| 7,833,189 | B2 | 11/2010 | Hunter et al. |
| 1,008,238 | A1 | 4/2011 | Hunter et al. |
| 1,016,654 | A1 | 7/2011 | Hunter et al. |
| 1,025,762 | A1 | 10/2011 | Hunter et al. |
| 1,031,193 | A1 | 12/2011 | Hunter |
| 8,105,270 | B2 | 1/2012 | Hunter |
| 8,172,790 | B2 | 5/2012 | Hunter et al. |
| 8,328,755 | B2 | 12/2012 | Hunter et al. |
| 2003/0083618 | A1 | 5/2003 | Angel et al. |
| 2004/0024364 | A1* | 2/2004 | Langley et al. ............ 604/187 |
| 2004/0106894 | A1 | 6/2004 | Hunter et al. |
| 2004/0260234 | A1 | 12/2004 | Srinivasan et al. |
| 2006/0258986 | A1 | 11/2006 | Hunter et al. |
| 2007/0129693 | A1 | 6/2007 | Hunter et al. |
| 2008/0009788 | A1 | 1/2008 | Hunter et al. |
| 2008/0281273 | A1 | 11/2008 | Angel et al. |
| 2009/0030285 | A1* | 1/2009 | Andersen ................ 600/300 |
| 2009/0240230 | A1* | 9/2009 | Azar et al. ............... 604/500 |
| 2010/0004624 | A1 | 1/2010 | Hunter |
| 2010/0016827 | A1 | 1/2010 | Hunter et al. |
| 2011/0054354 | A1 | 3/2011 | Hunter et al. |
| 2011/0054355 | A1 | 3/2011 | Hunter et al. |
| 2011/0143310 | A1 | 6/2011 | Hunter |
| 2012/0003601 | A1 | 1/2012 | Hunter et al. |
| 2012/0095435 | A1 | 4/2012 | Hunter et al. |
| 2012/0116212 | A1* | 5/2012 | Bral ....................... 600/424 |

FOREIGN PATENT DOCUMENTS

| | | |
|---|---|---|
| WO | WO-03/037404 A1 | 5/2003 |
| WO | WO-03/037405 A1 | 5/2003 |
| WO | WO-03/037406 A2 | 5/2003 |
| WO | WO-03/037407 A1 | 5/2003 |
| WO | WO-03/039635 A2 | 5/2003 |
| WO | WO-2004/021882 A2 | 3/2004 |
| WO | WO-2004/022138 A2 | 3/2004 |
| WO | WO-2006/086719 A1 | 8/2006 |
| WO | WO-2006/086720 A2 | 8/2006 |
| WO | WO-2006/086774 A2 | 8/2006 |
| WO | WO-2007/058966 A1 | 5/2007 |
| WO | WO-2008/027579 A1 | 3/2008 |
| WO | WO-2011/028716 A1 | 3/2011 |
| WO | WO-2011/028719 A2 | 3/2011 |
| WO | WO-2011/075535 A1 | 6/2011 |
| WO | WO-2011/075545 A1 | 6/2011 |
| WO | WO-2011/084511 A1 | 7/2011 |
| WO | WO 2012/048268 A2 | 4/2012 |
| WO | WO 2012/048277 A2 | 4/2012 |

OTHER PUBLICATIONS

Hemond, Brian D., et al., "Development and Performance of a Controllable Autoloading Neddle-Free Jet Injector," Journal of Medical Devices, Mar. 2011, vol. 5, pp. 015001-1-015001-7.

Stachowiak, Jeanne C., et al., "Dynamic control of needle-free jet injection," Journal of Controlled Release, Release 135 (2009), pp. 104-112.

Taberner, Andrew J., et al., "A Portable Neddle-free Jet Injector Based on a Custom High Power-density Voice-coil Actuator," Proceedings of the 28th IEEE, EMBS Annual International Conference, Aug. 30-Sep. 3, 2006, pp. 5001-5004.

Chen, K., et al., "A Needle-free Liquid Injection System Powered by Lorentz-force Actuator," *2010 International Conference on Mechanic Automation and Control Engineering (MACE2010)*, (Jun. 26-28, 2010).

Chen, K., and Zhou, H., "An experimental study and model validation of pressure in liquid needle-free injection," *Int'l Phy. Sci.*, 6(7):1552-1562 (Apr. 4, 2011).

International Preliminary Report on Patentability mailed on Apr. 18, 2013, in Application No. PCT/US2011/055454, "Injection Methods Using a Servo-Controlled Needle-Free Injector."

Invitation to Pay Additional Fees and, Where Applicable, Protest Fees mailed Feb. 28, 2012 in International Patent Application No. PCT/US2011/055454.

International Search Report and Written Opinion mailed Jul. 4, 2012 in International Patent Application No. PCT/US2011/055454.

Taberner, et al., "Needle-free jet injection using real-time controlled linear Lorentz-force actuators," *Med. Eng. Phys.*, (2012) doi: 10.1016/j.medengphy.2011.12.010.

* cited by examiner

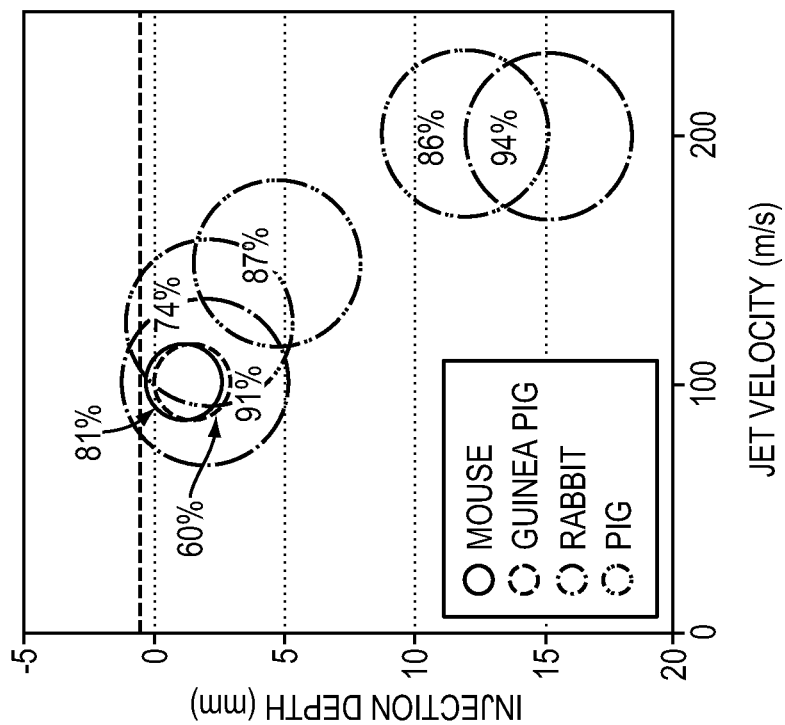
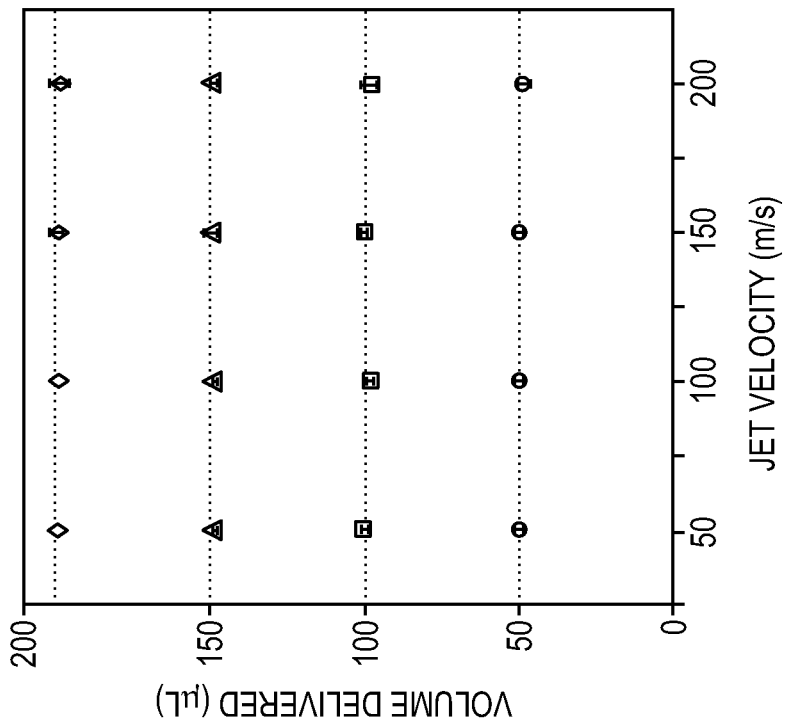
FIG. 9B
FIG. 9A

INJECTION METHODS USING A SERVO-CONTROLLED NEEDLE-FREE INJECTOR

RELATED APPLICATION

This application claims the benefit of and priority to U.S. provisional patent application Ser. No. 61/391,045, filed Oct. 7, 2010, the entirety of which is incorporated by reference herein.

FIELD OF INVENTION

This application relates generally to needle-free transdermal transport devices, particularly to methods of using servo-controlled needle-free devices and control systems therefor.

BACKGROUND

Injection of a liquid such as a drug into a human patient, an agriculture animal, or pet is performed in a number of ways. One of the easiest methods for drug delivery is through the skin, which is the outermost protective layer of the body. It is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue. It extends around 10-20 microns from the skin surface and has no blood supply. Because of the density of this layer of cells, moving compounds across the skin, either into or out of the body, can be very difficult.

The current technology for delivering local pharmaceuticals through the skin includes transdermal patches, ionotophoresis, sonophoresis, and methods that use needles or other skin piercing devices. Invasive procedures, such as use of needles or lances, effectively overcome the barrier function of the stratum corneum. However, these methods suffer from several major disadvantages: local skin damage, bleeding, risk of infection at the injection site, creation of contaminated needles or lances that must be disposed of, and compliance issues associated with fear of needles. Further, when these devices are used to inject drugs in agriculture animals, the needles can break off and remain embedded in the animal. Needle free injection technologies provide an effective alternative route for drug delivery devoid of many of the issues associated with delivery by more conventional methods. However, many of the currently commercially available technologies use actuators, for examples springs or compressed gases, that allow little to no control over the pressure exerted on the drug during delivery.

SUMMARY

In contrast to other needle-free devices, a needle-free injector including an electromagnetic actuator is capable of generating variable pressure profiles, with the current input determining the force and corresponding pressure generated at any given time. Further, an electromagnetic actuator configured in combination with a servo-controller permits tailoring of the pressure-time profile during an injection. This responsive feedback enables repeatable injection of precise volumes of pharmaceuticals through the skin and to specific depths in the tissue.

Beneficially, a servo-controlled needle-free injector includes an actuator capable of generating a high-speed, high-pressure pulse that is both controllable and highly predictable. Combined with a servo-controller receiving inputs from one or more sensors, the injector can tailor the pressure profile of the injection in real time during the course of the injection, in response to the sensed physical properties.

In an aspect, embodiments of an invention include a method for injecting a substance through a surface of a biological body. The method includes providing a needle-free transdermal transport device configured to inject the substance through the surface of the biological body. The substance is injected into the biological body with the transport device while (i) sensing a parameter associated with an injection including at least one of deformation of an ampoule disposed on the needle-free transdermal transport device, temperature of ambient, temperature of injected substance, sound of substance impinging on the biological body, and barometric pressure, (ii) using a servo-controller to dynamically adjust at least one injection characteristic based on the sensed parameter. The substance is injected for (i) a first time period during which a first portion of a volume of the substance is injected at a first injection pressure, and (ii) a second time period during which a remainder of the volume of the substance is injected at a second injection pressure.

One or more of the following features may be included. The orientation of the needle-free transdermal transport device with respect to the surface may be monitored using, for example, gyrometers and/or accelerometers. Sensing the parameter may further include sensing at least one of injection pressure, sensed pressure within the transport device, position, volume, mechanical impedance, force, current, and voltage. The at least one injection characteristic may be depth of injection and/or volume of injected substance. Prior to injecting the substance, the transport device may be pre-programmed with a jet velocity waveform. The jet velocity waveform may include a first jet velocity, the first time period, a second follow-through velocity, and the volume. The second time period may be determined by the needle-free transdermal transport device. The needle-free transdermal transport device may include a coil, and the injection characteristic may be dynamically controlled on the basis of measured coil displacement. The needle-free transdermal transport device may include a position sensor, and coil displacement may be measured by sensing the coil displacement with the position sensor.

In another aspect, embodiments of the invention include a method for injecting a substance through a surface of a biological body includes providing a needle-free transdermal transport device configured to inject the substance through the surface of the biological body. A viscosity of the substance is determined. A pressure for injecting the substance is calculated based on the determined viscosity. The substance is injected with the needle-free transdermal transport device by using the calculated pressure.

One or more of the following features may be included. The substance includes a viscous solution. The substance may include a polymeric material having at least one property that is temperature-dependent. The substance may include a biodegradable polymer allowing controlled release of a drug contained therein. Determining the viscosity of the substance may include at least one of (i) pre-programming the needle-free transdermal transport device with the viscosity, (ii) using the needle-free transdermal transport device to fill an ampoule with the substance, and calculating the viscosity on the basis of a force used to fill the ampoule, and/or (iii) sensing during the injection of the substance a change in at least one of pressure and velocity required for injection of the substance. The needle-free transdermal transport device may include a servo-controller, and the servo-controller may calculate the injection pressure based on the determined viscosity.

In another aspect, embodiments of the invention include a control system for a needle-free transdermal transport device configured to inject a substance through a surface of a biological body. The control system includes a sensor for sensing a parameter of the injection; and a servo-controller to dynamically adjust at least one injection characteristic based on the sensed parameter. The sensor and the servo-controller control the injection of the substance such that the substance is injected for (i) a first time period during which a first portion of a volume of the substance is injected at a first injection pressure, and (ii) a second time period during which a remainder of the volume of the substance is injected at a second injection pressure. The sensor may be a gyrometer, an accelerometer, a strain gauge, a temperature sensor, an acoustic sensor or transducer, and/or a barometric sensor.

BRIEF DESCRIPTION OF THE DRAWINGS

FIGS. 9A and 9B are graphs showing the controllability and repeatability of delivery volume, in accordance with an embodiment of the invention;

DETAILED DESCRIPTION

Figure 1:
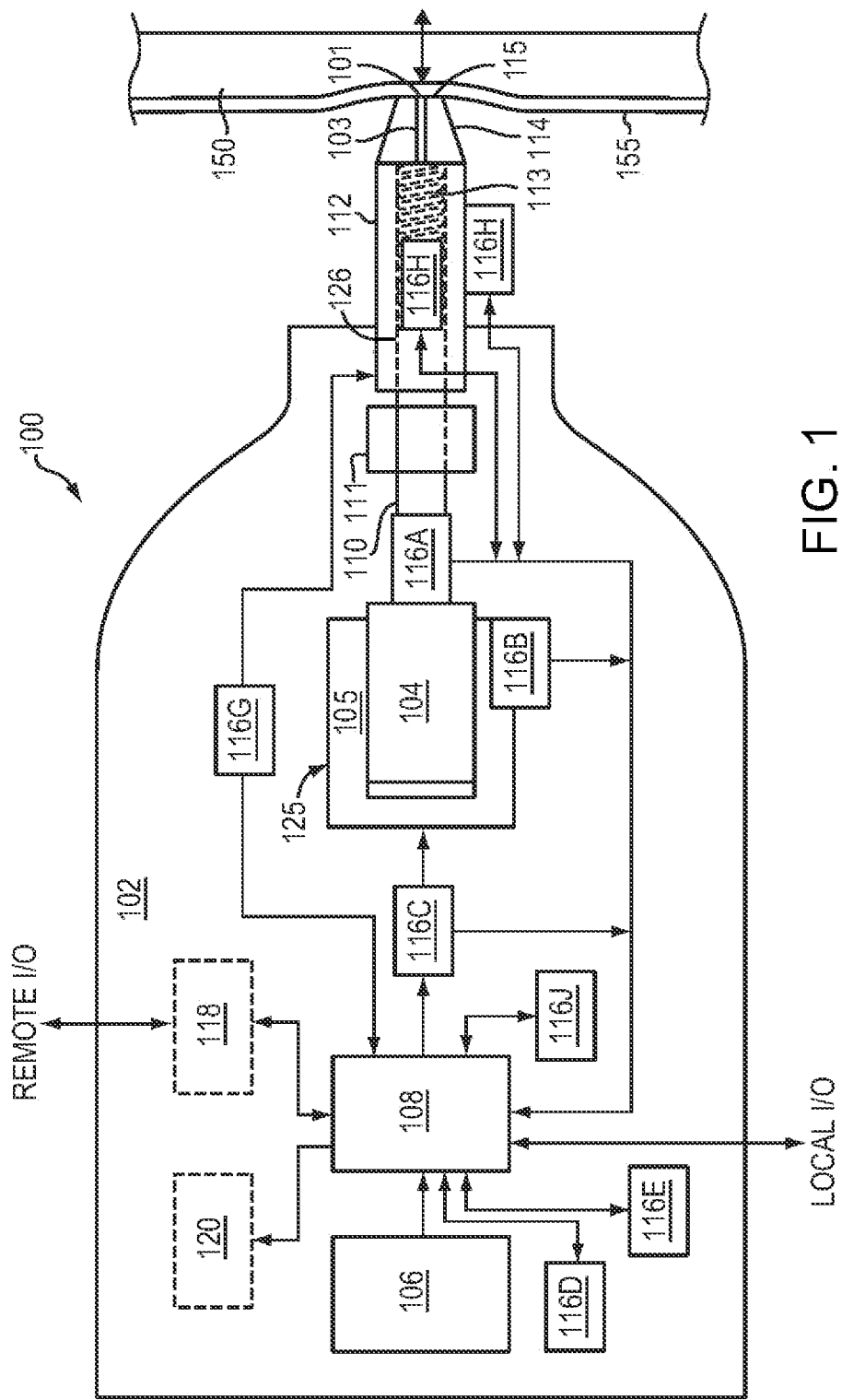
FIG. 1 is a schematic block diagram an exemplary controllable, needle-free transdermal transfer device (i.e., jet injector), suitable for use with embodiments of the invention.

Embodiments of methods of the invention may be practiced with a transdermal transport device, or injection device, configured to transfer a substance across a surface of a biological body. Injection devices include devices having one or more needles configured to pierce the skin prior to injection of the substance (e.g., typical hypodermic needle). Other injection devices are configured to inject a substance beneath the skin without first piercing the skin with a needle (i.e., needle-free). It should be noted that the term needle-free as used herein refers to devices that inject without first piercing the skin using a needle. Thus, needle-free devices may include a needle, but the needle is not used to first pierce the skin. Some needle-free injection devices rely on a pioneer projectile ejected from the device to first pierce the skin. Other needle-free injection devices rely on pressure provided by the impinging drug itself.

Injection devices generally include a reservoir or chamber for storing a substance to be injected (e.g., a drug). Injection devices also include a distal port through which the drug can be expelled to enter the body. The reservoir is typically in fluid communication with the distal port through a lumen. In operation, a pressure is applied to the reservoir forcing the drug through the lumen and out of the distal port. For needle-free applications, the distal port generally forms a nozzle through which the drug is expelled, forming a jet. The velocity of the jet may be sufficient to pierce the outer-most layer of skin and to penetrate the body to a desired depth.

A needle-free injector may be a closed-loop, servo-controlled device. An exemplary servo-controlled needle-free injector includes an electromagnetic pressure actuator in combination with a servo-controller that generates an injection pressure responsive in real-time to one or more physical properties (e.g., pressure, position, volume, etc.) The electromagnetic pressure actuator generates a high-pressure pulse having a rapid rise time (e.g., less than 1 millisecond) for injecting a formulation beneath the skin. The pressure provided by the actuator may be varied during the actuation of a single injection to achieve a desired result. For example, a first high pressure is initially provided to the formulation to penetrate the outer surface layer of an animal's skin. Once the skin is penetrated, the pressure is reduced to a second lower pressure for the remainder of the injection. The servo-controller can be used to determine when the skin is penetrated by sensing a change in pressure within the chamber and to adjust the injection pressure accordingly.

A servo-controlled needle-free injector includes one or more sensors, a servo controller, and a controllable actuator. One or more sensors are provided to measure respective physical properties, such as the position of the coil relative to a chamber, the resulting volume of the chamber and/or the pressure within the chamber. A servo-controller receives input signals from one or more sensors and generates an output signal according to a predetermined relationship. The servo-controller output can be used to control the pressure by controlling the amplitude of electrical current driving the controllable actuator.

Real time control can be accomplished by the servo controller repeatedly receiving inputs from the sensors, processing the inputs according to the predetermined relationship and generating corresponding outputs. In order to adjust the injection pressure during the course of an injection, the entire sense-control process is typically performed numerous times during the period of the injection. For example, a servo-controller can include a high-speed microprocessor capable of processing signals received from the sensors and rapidly providing corresponding output signals at a rate of 100 kHz (i.e., every 10 microseconds). Such rapid response times provide hundreds of opportunities to adjust pressure during the course of a single 5 to 10 millisecond injection.

One type of controllable actuator includes a conducting coil disposed relative to a magnetic field, such that an electrical current induced within the coil results in the generation of a corresponding mechanical force. The configuration is similar to that found in the voice coil of a loud speaker, the relationship between the magnetic field, the electrical current, and the resulting force being well defined and generally referred to as the Lorentz force. The actuator can be coupled to a piston acting upon a chamber containing a formulation. Alternatively or in addition, the actuator can be coupled to a bellows forming a chamber containing a formulation. For either configuration, actuation results in the generation of a pressure within the chamber, the chamber forcing the formulation through a nozzle. Other needle-free injection devices are either controllable in a very limited sense (e.g., spring actuators or gas discharge actuators), controllable in a feed forward sense (e.g., shape memory materials, such as Nitinol), or offer the possibility of closed-loop control (e.g., piezoelectric actuators) but are limited to injection volumes in the order of 1 to 10 µL and pose challenging scaling issues. An electrically driven linear Lorentz-force motor configured in combination with a servo-controller, offers closed-loop control without compromising stroke and is readily scaled.

Beneficially, a servo-controlled needle-free injector includes an actuator capable of generating a high-speed, high-pressure (or velocity) pulse that is both controllable and highly predictable. Combined with a servo-controller receiving inputs from one or more sensors, needle-free injector adjusts the pressure (or velocity) vs. time profile in real time during the course of an injection in response to sensed physical properties. Accordingly, an injection profile includes at least two distinct phases of delivery, a brief high pressure (or high velocity) phase required for penetration of the target followed by a slower follow-through pressure (or lower velocity) phase during which the bulk volume of substance is delivered; potentially reducing shear while permitting sufficient time for absorption into the tissue.

In some embodiments, the injector may be connected to a controller coupled with a skin sensor that detects skin properties. This information may be used to servo-control the needle-free injection to tailor the injection pressure (or velocity) and therefore the depth and penetration of drug into the skin for a particular application. Further, in some embodiments delivery waveform generation may be governed by a pressure transducer measuring, for example, pressure in the injection cylinder or ampoule.

In certain embodiments, servo-control may be based on a sequence of time for the injection, the injection profile being adjusted during delivery after a certain pre-determined amount of time has elapsed. In still other embodiments, the injection characteristics may be varied based on at least one of pressure, sensed pressure, and time.

Referring to FIG. 1, an exemplary needle-free transdermal transport device 100 with servo-control capability suitable for use with embodiments of the invention to transfer a substance across the surface 155 of a biological body 150 may be configured as follows. Although one type of device is described in detail, the method of the invention may be practiced with a wide range of needle-free transdermal transport devices, and is not limited to the exemplary device.

The device 100 may be used to inject a liquid formulation of an active principle, for example, a drug, into a biological body such as an agriculture animal or human being. Alternatively or in addition, the same device 100 may be used to collect a sample from a biological body 150 by withdrawing the collected sample through the surface 155 of the body and into an external reservoir 113 that may be provided within the device 100.

The device 100 typically includes a nozzle 114 to convey the substance through the surface 155 of the biological body at the required speed and diameter to penetrate the surface 155 (e.g., skin) as required. The substance ejected from the nozzle 114 forms a jet, the force of the jet determining the depth of penetration. The nozzle 114 generally contains a flat surface, such as the head 115 that can be placed against the skin, and forms an orifice 101. The inner diameter of the orifice 101 controls the diameter of the transferred stream. Additionally, the length of an aperture, or tube 103, defining the orifice 101 also controls the transfer (e.g., injection) pressure.

The nozzle 114 may be coupled to a syringe 112 defining a reservoir 113 for temporarily storing the transferred substance. The syringe 112 may include a plunger or piston 126 having at least a distal end slidably disposed within the reservoir 113. Movement of the plunger 126 along the longitudinal axis of the syringe 112 in either direction creates a corresponding pressure within the reservoir 113. For example, a commercially-available needle-free syringe 112 can be attached to the device 100, such as a model reference no. 100100 syringe 112 available from Equidine Systems Inc. of San Diego, Calif.

Beneficially, a pressure is selectively applied to the chamber 113 using a controllable actuator. Electromagnetic actuator 125 is configured to generate a high-pressure pulse having a rapid rise time (e.g., less than 1 millisecond). The actuator is dynamically controllable, allowing for adjustments to the pressure-versus-time during actuation.

The electromagnetic actuator 125 is configured to provide a linear force applied to the plunger 126 to achieve transdermal transfer of the substance. Transfer of the force can be accomplished with a force-transfer member 110, such as a rigid rod slidably coupled through a bearing 111.

The actuator 125 may include a stationary component, such as a magnet assembly 105, and a moveable component, such as coil assembly 104. A force produced within the coil assembly 104 may be applied to the plunger 126 directly or indirectly through the rod 110 to achieve transdermal transfer of the substance. Generally, the actuator 125, bearing 111 and syringe 112 are coupled to a frame or housing 102 that provides support and maintains fixed position of these elements during an actuation.

The device 100 may include a user interface 120 that provides a status of the device. The user interface may provide an indication that the device is ready for an actuation. For example, a light emitting diode (LED) coupled to a controller 108 may be enabled when sufficient conditions are satisfied for an injection. User interfaces 120 may include any suitable technology capable of conveying detailed information between a user and the device 100. The user interface 120 may also enable an operator to provide inputs as user selections for one or more parameters. Thus, a user may identify parameters related to dose, sample, and/or the biological body, such as age, weight, etc.

A power source 106 provides an electrical input to the coil assembly 104 of the actuator 125. An electrical current applied to the coil assembly 104 in the presence of a magnetic field provided by the magnet assembly 105 results in a generation of a mechanical force capable of moving the coil assembly 104 and exerting work on the plunger 126 of the syringe 112.

The controller 108 is electrically coupled between the power source 106 and the actuator 125. The controller 108 can selectively apply, suspend and otherwise adjust the electrical input signal provided by the power source 106 to the actuator 125. The controller 50 may be a simple switch operable by a local interface. For example, a button provided on the housing 102 may be manipulated by a user, selectively applying and removing an electrical input from the power source 106 to the actuator 125. The controller 108 may control elements, such as electrical circuits, that are adapted to selectively apply electrical power from the power source 106 to the actuator 125, the electrical input being shaped by the selected application.

The needle-free transdermal transport device 100 may include a remote interface 118. The remote interface 118 may be used to transmit information, such as the status of the device 100 or of a substance contained therein to a remote source. Alternatively or in addition, the remote interface 118 may be in electrical communication with the controller 108 and may be used to forward inputs received from a remote source to the controller 108 to affect control of the actuator 125.

The remote interface 118 can include a network interface, such as a local area network interface, a wide-area network interface, a modem or a wireless interface capable of interfacing with a remote device/user over a public-switched telephone network.

The controller 108 may receive inputs from one or more sensors adapted to sense a respective physical property. For example, the device 100 includes a transducer, such as a position sensor 116B to indicate location of an object's coordinates (e.g., the coil's position) with respect to a selected reference. Similarly, a displacement may be used to indicate movement from one position to another for a specific distance. Beneficially, the sensed parameter can be used as an indication of the plunger's position as an indication of dose. A proximity sensor may also be used to indicate a portion of the device, such as the coil, has reached a critical distance. This may be accomplished by sensing the position of the plunger 126, the force-transfer member 110, or the coil assembly 104 of the electromagnetic actuator 125. For example, an optical sensor such as an optical encoder can be used to count turns of the coil to determine the coil's position. Other types of sensors suitable for measuring position or displacement include inductive transducers, resistive sliding-contact transducers, photodiodes, and linear-variable-displacement-transformers (LVDT).

Other sensors, such as a force transducer 116A, may be used to sense the force applied to the plunger 126 by the actuator 125. As shown, a force transducer 116A can be positioned between the distal end of the coil assembly and the force transfer member 110, the transducer 116A sensing force applied by the actuator 125 onto the force transfer member 110. As this member 110 is rigid, the force is directly transferred to the plunger 126. The force tends to move the plunger 126 resulting in the generation of a corresponding pressure within the reservoir 113. A positive force pushing the plunger 126 into the reservoir 113 creates a positive pressure tending to force a substance within the reservoir 113 out through the nozzle 114. A negative force pulling the plunger 126 proximally away from the nozzle 114 creates a negative pressure or vacuum tending to suck a substance from outside the device through the nozzle 114 into the reservoir 113. The substance may also be obtained from an ampoule, the negative pressure being used to pre-fill the reservoir 113 with the substance. Alternatively or in addition, the substance may come from the biological body representing a sampling of blood, tissue, and or other interstitial fluids. A pressure transducer (not shown) can also be provided to directly sense the pressure applied to a substance within the chamber.

An electrical sensor 116C may also be provided to sense an electrical input provided to the actuator 125. The electrical sensor 116C may sense one or more of coil voltage and coil current. Other sensors may include, for example, a gyrometer 116D, an accelerometer 116E, a strain gauge 116F, a temperature sensor 116G, an acoustic sensor or transducer 116H, and/or a barometric sensor 116J. The sensors 116A, 116B, 116C, 116D, 116E, 116F, 116G, 116H, and 116J (generally 116) are coupled to the controller 108 providing the controller 108 with the sensed properties. The controller 108 may use one or more of the sensed properties to control application of an electrical input from the power source 106 to the actuator 125, thereby controlling pressure generated within the syringe 112 to produce a desired transfer performance. For example, a position sensor can be used to servo-control the actuator 125 to pre-position the coil assembly 104 at a desired location and to stabilize the coil 104 once positioned, and conclude an actuation cycle. Thus, movement of the coil assembly 104 from a first position to a second position corresponds to transfer of a corresponding volume of substance. The controller can include a processor programmed to calculate the volume based on coil position give the physical size of the reservoir.

An actuation cycle generally corresponds to initiation of an electrical input to the actuator 125 to induce transfer of a substance and conclusion of the electrical input to halt transfer of the substance. A servo-control capability combined with the dynamically controllable electromagnetic actuator 125 enables adjustment of the pressure during the course of an actuation cycle. One or more of the sensors 116 can be used to further control the actuation cycle during the course of the transfer, or cycle. Alternatively or in addition, one or more of local and remote interfaces can also be used to further affect control of the actuation cycle.

The controller 108 may be coupled with one or more other sensors (not shown) that detect respective physical properties of the biological surface. This information may be used to servo-control the actuator 125 to tailor the injection pressure, and, therefore, the depth of penetration of drug into the skin for a particular application. Moreover, the injection pressure may be varied over time.

Figure 2A:
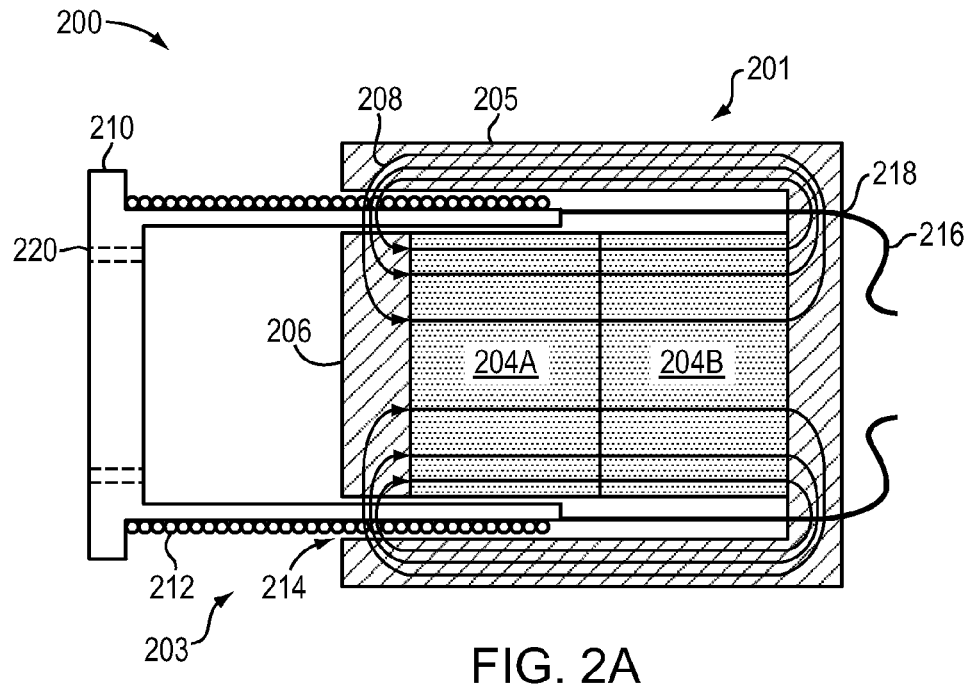
FIGS. 2A and 2B are cross-sectional diagrams of a controllable electromagnetic actuator usable with the device of FIG. 1, shown in extended and retracted configurations, respectively.

A cross-sectional diagram of an electromagnetic impulse actuator 200 is shown in FIG. 2A. The device 200 includes a magnet assembly 205 defining an annular slotted cavity 214 and a coil assembly 203 slidably disposed therein. The stroke of the coil 203 may be controlled by the lengths of the coil and magnet assembly.

The magnet assembly 205 includes a column of magnets 204A, 204B disposed along a central axis. The column of magnets may be created by stacking one or more magnetic devices, such as permanent magnets. A suitable category of strong, high-density magnets are rare-earth magnets, also known as Neodymium-Iron-Boron magnets (e.g., $Nd_2Fe_{14}B$), such as N50 magnets. The magnetic field produced by the magnets generally follows field lines 208.

The magnets 204A, 204B are attached at one end of a right-circular cylindrical shell 201 defining a hollowed axial cavity and closed at one end. An annular slot remains being formed between the magnets 204A, 204B and the interior walls of the case and accessible from the other end of the shell 201. An exemplary shell 201 is formed with an outside diameter of about 40 mm and an inside diameter of about 31.6 mm, resulting in a wall thickness of about 4.2 mm. The magnets 204A, 204B may be cylindrical, having a diameter of about 25.4 mm.

The shell 201 is preferably formed from a material adapted to promote containment of the magnetic fields produced by the magnets 204A, 204B. For example, the shell 201 may be formed from a ferromagnetic material or a ferrite. One such ferromagnetic material includes an alloy referred to as carbon steel (e.g., American Iron and Steel Institute (AISI) 1026 carbon steel). An end cap 206 is also provided of similar ferromagnetic material being attached to the other end of the magnets 204A, 204B. Placement of the end cap 206 acts to contain the magnetic field therein and promoting a radially-directed magnetic field between the annular gap formed between the end cap 206 and the outer walls of the shell 201. The end cap is generally thicker than the shell walls to promote containment of the magnetic fields as they loop into the end of the top magnet 204A. For the exemplary shell 201 described above, the end cap 206 has an axial thickness of about 8 mm.

The coil assembly 203 includes a coil 212 formed from a conducting material, such as copper wire wound about a bobbin 210. The bobbin 210 can be cylindrical and defines an axial cavity sized to fit together with the coil 212 within the annular cavity 214. The bobbin 210 may be substantially closed at the end juxtaposed to the annular cavity 214. The closed end forms a force-bearing surface adapted to push against a plunger 214 or force-bearing rod 210.

A strong, yet light-weight coil assembly 203 is preferred for applications requiring a rapid generation of substantial force, such as needle-free transfers. Preferably, the bobbin 210 is formed from a strong, yet light-weight readily machinable material, for example poly-acetal resins which are particularly well-suited for high temperature applications.

The bobbin 210 is thin-walled to fit within the annular slot. A thin-walled bobbin 210 allows for a narrower annular slot 214 thereby promoting a greater magnetic field intensity across the gap.

The bobbin 210 may have an outside diameter of about 27 mm, an internal diameter of about 26 mm, and an axial length of about 46 mm. The coil 212 consists of six layers of 28 gauge copper wire wound onto the bobbin 210 at a rate of about 115 windings per coil length (about 35 mm) resulting in about 700 turns total. Using the N50 magnets with the 1026 carbon steel, the end cap 206 contains between about 0.63 and 0.55 Tesla (the value reducing outwardly along a radius measured from the center of the end cap 206).

Thus, a current flowing through the coil 212 is positioned at right angles to the magnetic field 208 produced between the end cap 206 and the shell 201 wall. This results in the generation of a force on the coil directed along the longitudinal axis, the direction of the force depending upon the directional flow of the current. For the above exemplary device, an electrical input, or drive voltage of about 100 volts is applied across the coil for a duration of about 1 millisecond representing the pierce phase of an actuation cycle. A lesser electrical input of about 2-5 volts is applied for the transfer phase.

Generally, the coil 212 receives the electrical input signal through two electrical leads 216. The shell 201 includes one or more apertures 218 through which the leads 216 are routed to the power source 106 (FIG. 1). The closed end of the shell 201 may contain one or more additional apertures through which air may be transferred during movement of the coil. Without such apertures and given the relative tight tolerances of the gap between the coil 212 and the annular slot 214, a pressure would build up to oppose movement of the coil. Alternatively or in addition, the bobbin 210 may also have one or more apertures 220 to further inhibit the build up of damping pressures during actuation.

Figure 2B:
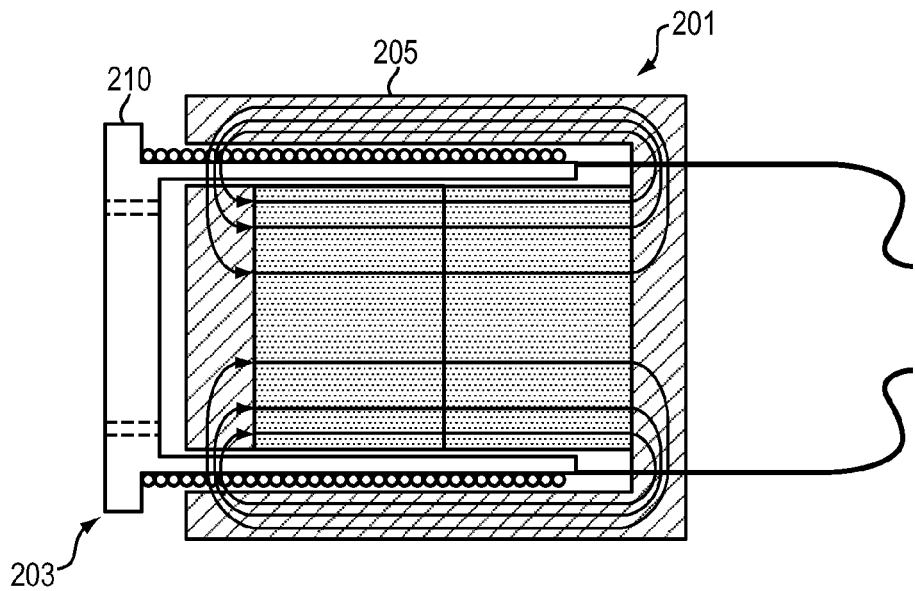

FIG. 2A shows the coil assembly 203 after or during an injection phase in which the coil is forced out of the shell 201 thereby advancing the front plate 215. FIG. 2B shows the coil assembly 203 retracted within the shell 201 after a sampling phase in which the coil assembly 203 is drawn into the shell 201.

The conductive coil may be configured to carry a relatively high-amplitude electrical current to produce a substantial force resulting in the generation of a substantial pressure. The coil also provides a relatively low inductance, e.g., less than 100 millihenries to support high-frequency operation. One way to provide high-current capacity with the low inductance is using a coil formed by a large-diameter conductor that is configured with a low number of turns (e.g., 1 to 3 turns).

The result is a pressure actuator capable of generating a high-pressure pulse with a rapid rise time. Additionally, operation of the actuator is both controllable and highly predictable given the physical properties of the actuator and the input electrical current. Still further, the actuator is reversible providing forces in opposing directions based on the direction of current flow within the coil.

Figure 3A:
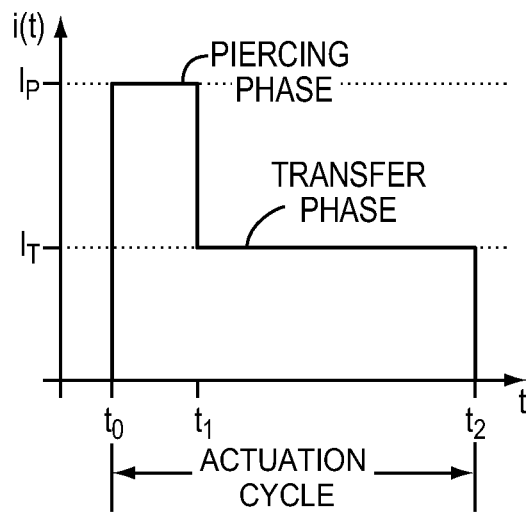
FIG. 3A is a graph depicting a current-versus-time profile of an exemplary electrical input to the controllable electromagnetic actuator of FIGS. 2A-2B.

Additionally, the controllability allows for a tailored injection profile that can include a rapid high-pressure pulse to breach the outer layers of skin, followed by a lower-pressure, prolonged pulse to deliver the formulation. Referring to FIG. 3A, an exemplary time varying electrical input is shown. The curve represents variation in an electrical current applied to the coil assembly 104 of the actuator 125. At a first instant of time $t_0$ an electrical current is applied to the coil 104. The current rises from a rest value (e.g., zero amps) to a maximum value $I_P$ remaining at this maximum for a selectable duration and then transitioning to a different current value $I_T$ at a later time $t_1$. The current amplitude may remain substantially at this value, or continue to vary with time until a later time $t_2$, at which the current returns to a rest value.

The entire period of time defined between times $t_2$ and $t_0$ can be referred to as an actuation period, or actuation cycle. For a current input having a shape similar to that just described, the period defined between times $t_1$ and $t_0$ can be referred to as a piercing phase. As the name suggests, the high current value $I_p$ induces a corresponding high pressure that can be used to pierce the surface of a biological body without using a needle or lance. The remainder of the actuation cycle defined between times $t_2$ and $t_1$ can be referred to as a transfer phase. As this name suggests, the relatively lower current value $I_T$ induces a lesser pressure that can be used to transfer a substance from the reservoir 113 (FIG. 1) to the biological body through the perforation in the surface created during the piercing phase.

Figure 3B:
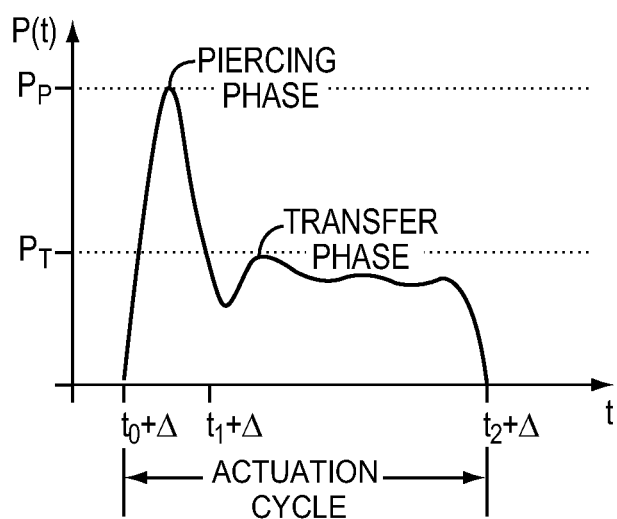
FIG. 3B is a graph depicting a pressure-versus-time profile of an exemplary pressure generated within a reservoir used in the transfer of a substance, the pressure being generated by the controllable electromagnetic actuator responsive to the electrical input of FIG. 3A.

An exemplary plot of a pressure induced within the reservoir 113 (FIG. 1) in response to the electrical input is illustrated in FIG. 3B. As shown, the pressure rises from an initial rest value to a relative maximum value, $P_p$, at a time $t_0$, perhaps with a slight delay $\Delta$ resulting from the transfer characteristics of the electrical coil. This pressure value can be used to create a jet as described above in relation to FIG. 1. As the current is reduced during the transfer phase, the pressure similarly reduces to a lesser value $P_T$ determined to achieve a desired transfer of the substance. The transfer phase continues until a desired volume of the substance is transferred, then the pressure is removed concluding the actuation cycle.

A servo-controlled injector includes a specially-designed electromagnetic pressure actuator configured in combination with a servo controller to generate an injection pressure responsive in real-time to one or more physical properties (e.g., pressure, position, volume, etc.). In some embodiments, the servo-controlled injector is a needle-free device. The electromagnetic pressure actuator generates a high-pressure pulse having a rapid rise time (e.g., less than 1 millisecond) for injecting a formulation beneath the skin. With such a rapid rise time, an entire transfer can be completed in less than about 10 milliseconds. The pressure provided by the actuator can be varied during the actuation of a single injection to achieve a desired result. For example, a first high-pressure is initially provided to the formulation to penetrate the outer surface layer of an animal's skin. Once the skin is penetrated, the pressure is reduced to a second, lower pressure for the remainder of the injection. The servo-controller can be used to determine when the skin is penetrated by sensing a change in pressure within the chamber and to adjust the injection pressure accordingly.

A servo-controller 108 receives input signals from the one or more sensors 116 and generates an output signal according to a predetermined relationship. The servo-controller output can be used to control the pressure by controlling the amplitude of electrical current driving the controllable actuator.

Real-time control can be accomplished by the servo controller 108 repeatedly receiving inputs from the sensors 116, processing the inputs according to the predetermined relationship and generating corresponding outputs. In order to adjust the injection pressure during the course of an injection, the entire sense-control process is preferably performed numerous times during the period of the injection. For example, a servo-controller 108 can include a high-speed microprocessor capable of processing signals received from the sensors and rapidly providing corresponding output signals at a rate of 100 kHz (i.e., every 10 microseconds). Such rapid response times provide hundreds of opportunities to adjust pressure during the course of a single 5 to 10 millisecond injection.

Figure 4:
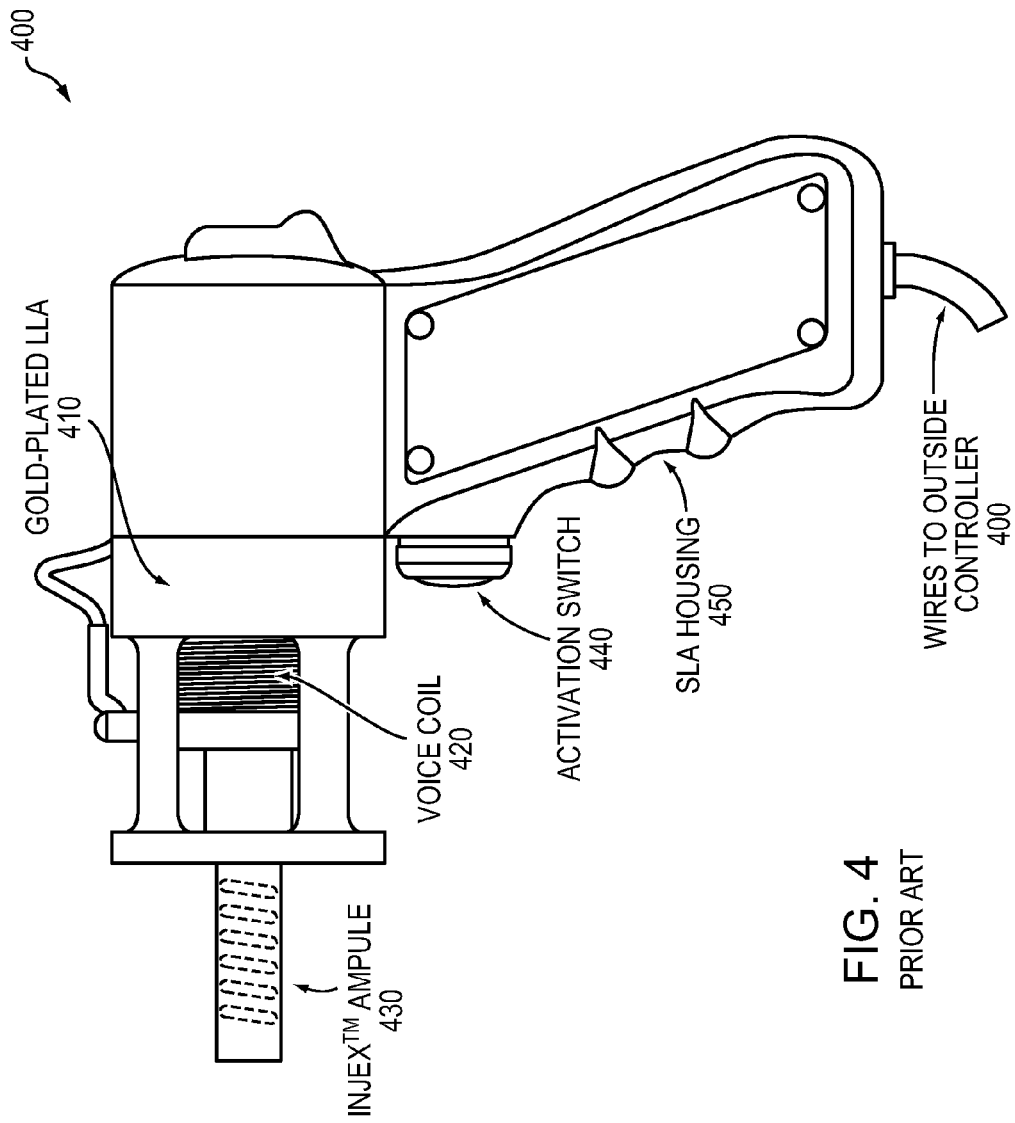
FIG. 4 is a photograph of an exemplary handheld servo-controlled jet injector that may be used with the present invention.

Referring to FIG. 4, a servo-controlled jet injector suitable for use with embodiments of the invention includes a handheld injector 400, a real-time controller (not shown), and a linear power amplifier The hand held injector 400 comprises a voice coil 420 that slides freely along a steel extrusion as it moves in the motor 410, an ampoule such as the commercially available disposable Injex™ 30 ampoule 430 (0.3 mL; part #100100 available from Injex-Equidyne Systems, Inc., based in Fullerton, Calif.), a push button activation switch 440, housing 450 that surrounds the interior components of the injector, and wires 460 that connect to a controller.

Figure 5:
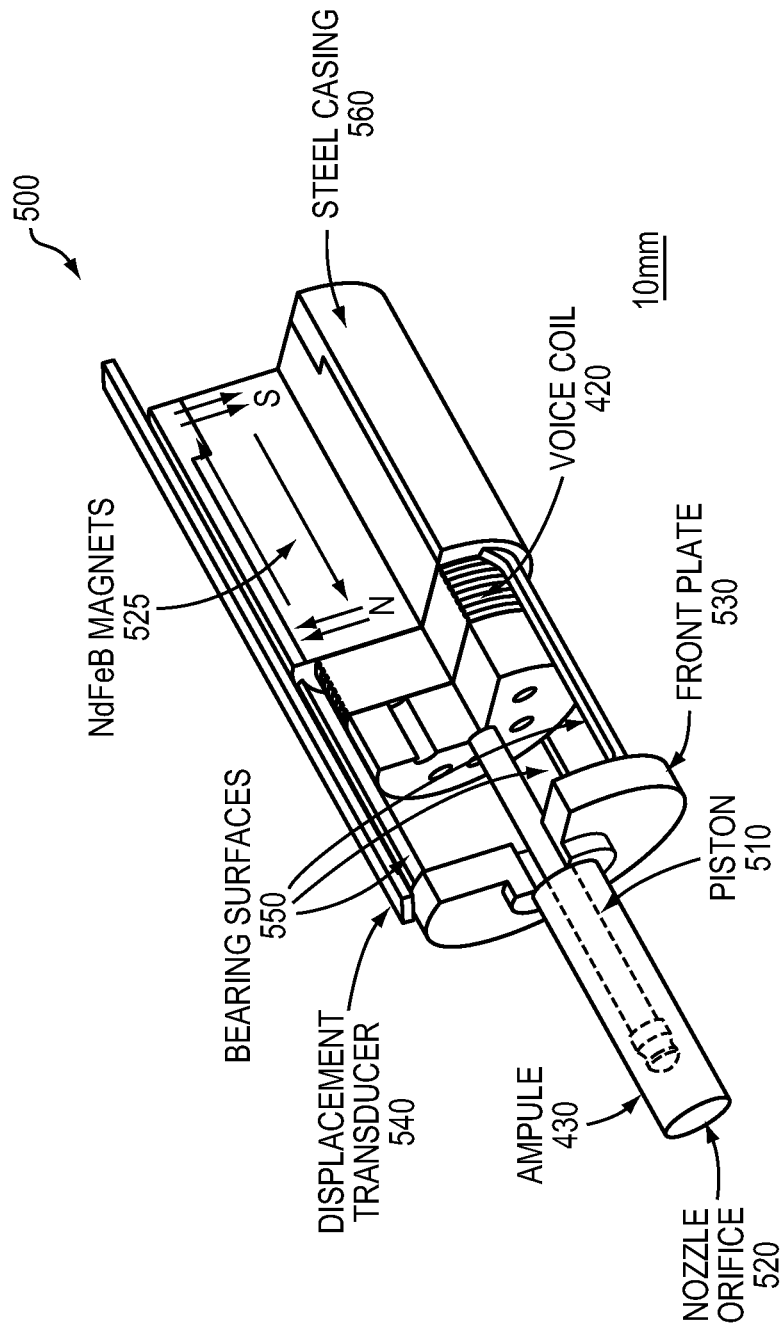
FIG. 5 is a cut-away schematic view of a controllable electromagnetic actuator suitable for use with the device of FIG. 4.

In the cut-away shown in FIG. 5, the Injex™ 30 ampoule 430 is screwed into a front plate 535 of the jet injector and the piston 510 is threaded into the front of the moving coil 420. The choice of ampoule may be based on availability, relatively low cost, proven performance, and ease with which it may be adapted for inclusion into the injection device. The internal diameter of the ampoule may taper at the tip to form a nozzle orifice 520 having a diameter of, e.g., 220±5 μm. In the illustrated embodiment, a delivery volume of 300 μL is realized with a 30 mm stroke.

The custom-designed linear Lorentz-force motor consists of 582 turns of 360 μm diameter enameled copper wire wound six layers deep on a custom-designed, thin-walled former. The former may be machined from polyetherimide stock; the material choice that permits minimization of the moving mass (~50 g) and avoids the drag incurred by induction of eddy currents in a conducting former. Current applied to the copper wire creates an axial Lorentz force of up to 200 N with a force constant of 10.8±0.5 N/A. The total DC resistance of the coil may be approximately 11.3Ω.

The voice coil 420 slides freely and smoothly on the bearing surfaces 550 and inside a 1026 carbon-steel extrusion casing 560 that also forms the magnetic circuit. The latter may include two 0.4 MN/m$^2$ (50 MGOe) NdFeB magnets 525 inserted into the casing. The magnetic flux density in the field gap may be approximately 0.6 Tesla.

Plastic-laminated, flexible copper ribbons may form the electrical connections to the coil. A 10 kΩ linear potentiometer (i.e., displacement transducer) 540 with >1 kHz bandwidth may be mounted to the linear guide system to monitor the position of the coil. The position sensor may be coupled to the coil via a movable pin that is mounted on the leading edge of the former. The system may be powered by a 4 kW Techron amplifier, controlled by a PC-based data acquisition and control system running in National Instruments Labview™ 8.5, which allows the testing of a variety of waveforms and concomitant evaluation of both the current and displacement.

High-speed position monitoring and servo-control of coil position is achieved using a compact reconfigurable system comprising a real-time controller (e.g., cRIO-9004, National Instruments, Austin, Tex.) embedded in a reconfigurable field-programmable gate-array (FPGA) chassis (cRIO-9104). The controller may execute a LabVIEW 8.5 Real-Time "host" application that interacts with the FPGA circuitry, performs high-level injection trajectory planning, interprets user commands, and provides real-time and post-injection feedback. The user interface of the host application may be broadcast by a web-server running on the controller, and operated from a web-browser on a networked laptop computer.

Figure 6:
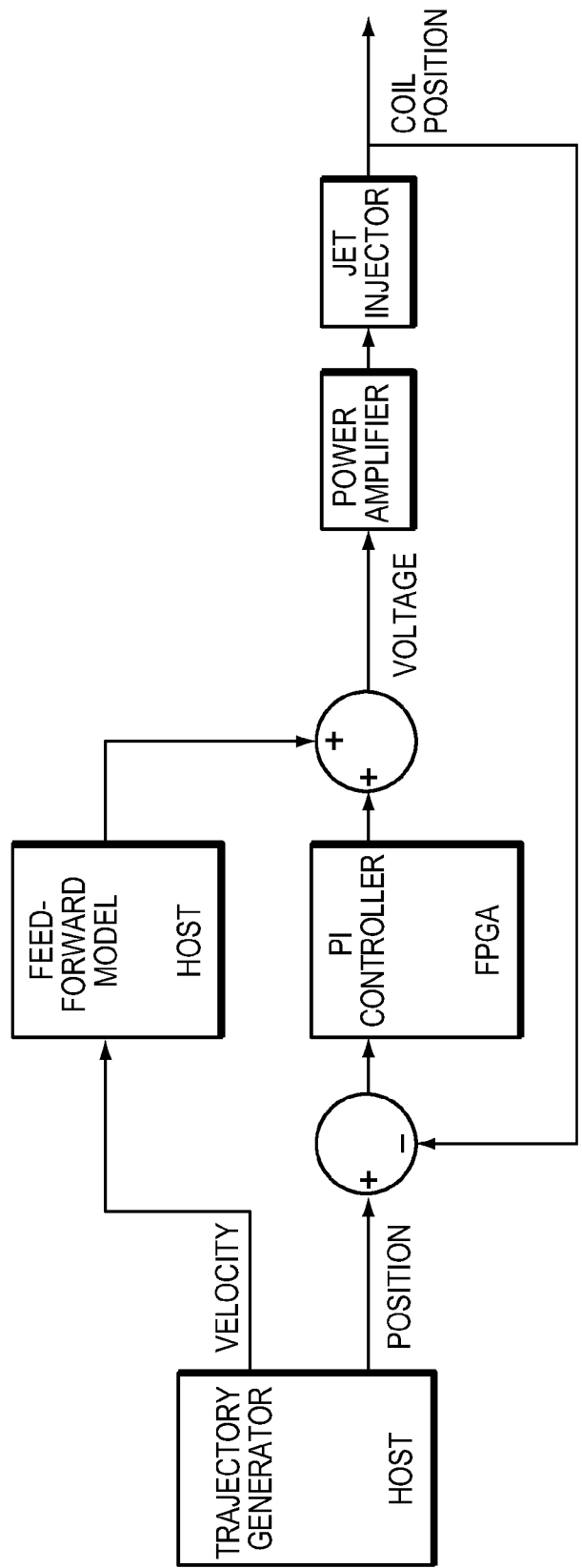
FIG. 6 is a block diagram of an exemplary control system architecture suitable for use with the device of FIG. 4.

The position-based jet-injector control algorithm has two components: (i) a velocity-driven feed-forward (FF) model that predicts the voltage required to achieve a given jet-speed, and (ii) a linear proportional-integral (PI) displacement feedback controller to counteract noise and disturbances to the injector system, as depicted in FIG. 6. Both components are active when the coil is in motion; FF dominates during injections while the feedback dominates during refilling and holding and ensures that the correct volume of fluid is delivered.

Injection waveforms (or trajectories) are generated with two distinct phases of delivery: a brief high-speed phase followed by a second lower speed phase of variable duration. The first phase accelerates the coil to the desired jet velocity ($V_{jet}$) required for penetration where it is maintained for a pre-determined period of time ($T_{jet}$) after which the coil is gently decelerated to a lower follow-through velocity ($V_{ft}$). This velocity is maintained until the coil position approaches the displacement at which the desired injection volume (V) is realized. Feedback of jet speed is implicit from position feedback, with the derivative or slope of the coil vs. time plot representing velocity. The integral of the position vs. time plot yields the volume being delivered.

A variety of additional sensors may be used to provide information to facilitate delivery using the jet injector. Position/orientation of the device prior to and during delivery may be provided using gyrometers and accelerometers. Information about the device/material interface may be supplied using acoustic sensors. Inclusion of strain gauges and temperature sensors may provide information about the pressures and forces required to deliver substance across a biological body as would sensors measuring force, position, and current or voltage. In a preferred embodiment, coil position may be monitored. The position-based control algorithm has two components: (i) a velocity-driven feed forward model and (ii) a linear proportional-integral displacement feedback controller to counteract noise and disturbances to the injector system, as depicted in FIG. 6. Both components are active when the coil is in motion; FF dominates during injections while the feedback dominates during refilling and holding and ensures that the correct volume of fluid is delivered.

The voltage applied to the coil imposes a corresponding force on the piston that generates a fluid pressure sufficient to deliver a defined volume of fluid to the target using the user-defined velocity profile. Feedback of jet speed is implicit from position feedback, with the derivative or slope of the coil vs. time plot representing velocity. The integral of the position vs. time plot yields the volume being delivered. In this embodiment, the operator defines and previews a jet velocity waveform (or trajectory) prior to injection in terms of four parameters:

the desired jet velocity ($V_{jet}$) required to penetrate the target,
the time at jet velocity ($T_{jet}$),
a typically slower follow-through velocity ($V_{ft}$), and
the total injection volume (V).

During the initial phase of delivery, the coil is accelerated to a speed that achieves the desired $V_{jet}$, which is maintained for the user defined $T_{jet}$ and then gently decelerated to the desired $V_{ft}$ speed. The $V_{ft}$ is maintained until the coil position approaches the displacement at which the desired injection volume is realized.

The injection of the fluid has the following characteristics. The feedback control system controls the ejected volume of drug during the time-course of injection using feedback from the measured coil displacement. Delivery of a constant volume at variable jet speed and constant $V_{ft}$ speed affects the total time required for delivery. Similarly, delivery of variable volume at a constant jet speed and constant $V_{ft}$ speed affects the total time required for delivery. The depth of the erosion hole is determined by the initial high velocity phase of the injection. Tight control of the piston velocity permits electronic selection of the injection depth by varying $V_{jet}$ or $T_{jet}$.

Figure 7B:
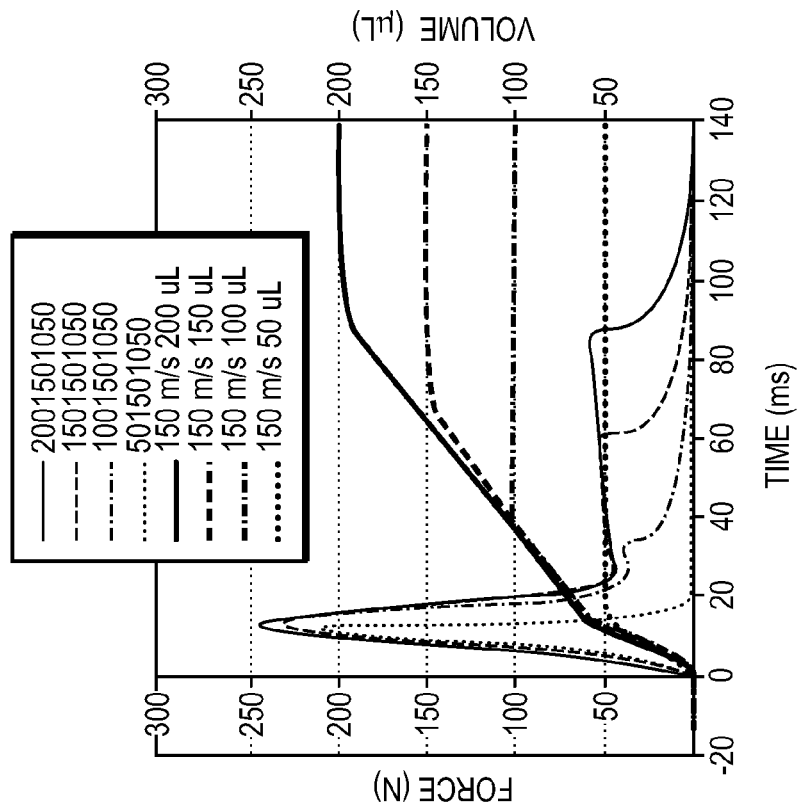
FIGS. 7A and 7B are graphs illustrating the effects of varying applied force and thereby the velocity at which fluid is delivered and the volume of fluid delivered, respectively, in accordance with an embodiment of the invention.
Figure 7A:
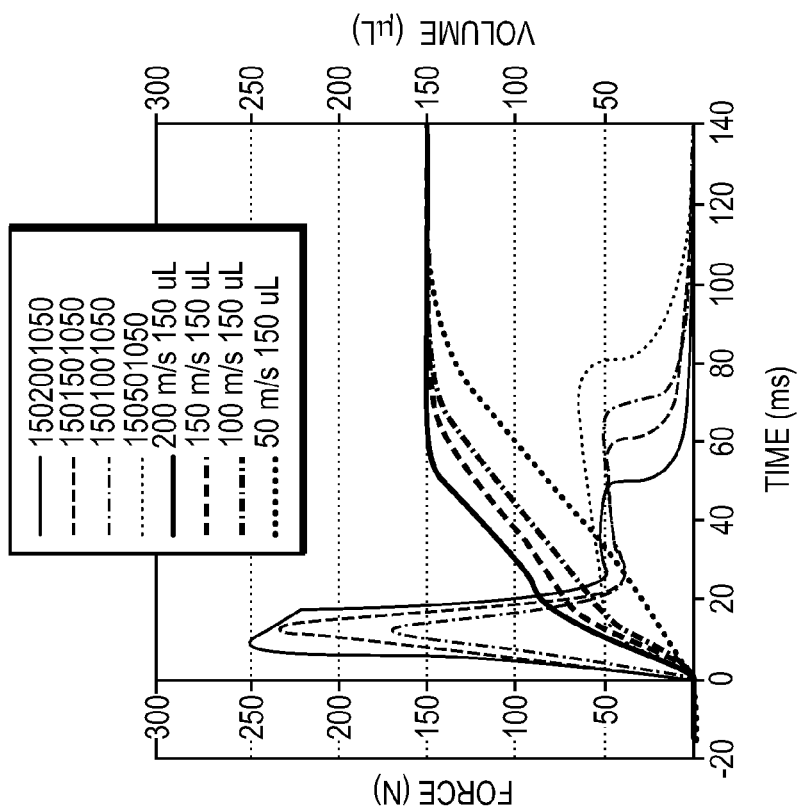

In particular, FIGS. 7A and 7B are graphs showing the effects of varying the applied force and thereby the velocity at which fluid is delivered and the volume of fluid delivered, respectively. FIG. 7A illustrates that ejection of a constant volume of fluid using variable jet velocity when $T_{jet}$ and $V_{ft}$ are held constant alters the duration of the injection. With increasing jet velocity, the volume of fluid delivered at $V_{jet}$ increases leaving less fluid to be delivered during $V_{ft}$ with the desired volume being delivered over a shorter time period. As can be seen in FIG. 7B, at constant jet velocity and follow-through velocity, an increase in the volume of fluid to be delivered results in a corresponding increase in the time required for delivery, as expected. The line of numbers in each legend (e.g., 1502001050) refer to the parameters used for delivery; the first three numbers referencing the volume of fluid delivered in microliters, the next three numbers referencing the jet velocity in m/s, the next two numbers referencing the time at jet velocity in ms, and the final two numbers referencing the follow-through velocity in m/s.

Figure 8B:
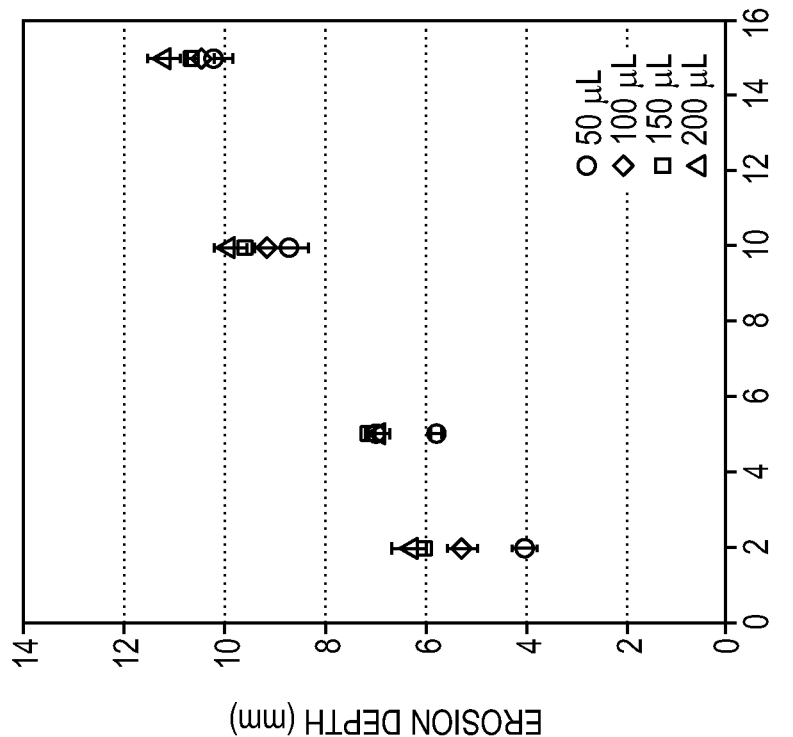
FIGS. 8A and 8B are graphs illustrating injection depth into tissue analogue, modified by varying the jet speed or time at jet speed, in accordance with an embodiment of the invention.
Figure 8A:
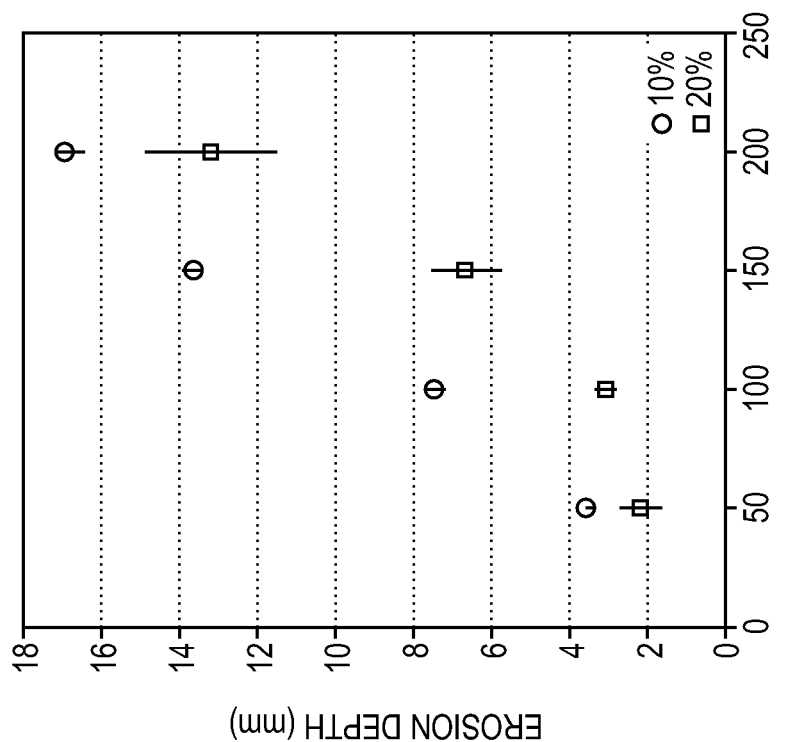

FIGS. 8A and 8B are graphs generated using servo-controlled jet injection, showing that both the jet velocity and the time for which jet velocity is maintained influence penetration (i.e., erosion) depth. For 10% acrylamide gels, penetration depth is linearly related ($R^2=0.99$) to jet speed while injection into 20% acrylamide gels was non linear; with penetration depth at a given jet velocity being more variable as shown in FIG. 8A. Modulating the time at jet velocity ($T_{jet}$) while holding the jet velocity and follow-through velocity constant resulted in an increase in penetration depth as shown in FIG. 8B.

FIGS. 9A and 9B are graphs showing the controllability and repeatability of delivery volume using the servo-controlled jet injector. The graph of FIG. 9A illustrates volume (as determined by weight) of fluid delivered to vials as a function of increasing jet velocity. The error bars represent the mean and standard deviations, respectively, of 24 ejections. FIG. 9A indicates tight control over the volume (as determined by weight) of repeated ejections of a subset of the ampoule contents into vials with increasing jet speed. The system is capable of ejecting a mean volume of fluid that equates to 99.18±0.04% (σ±se) of the target volume with a coefficient of variation (quantified across 24 ejections) of typically better than 0.01.

FIG. 9B shows delivery of typically >80% of fluid to the target tissue; repeatable delivery volume being effected by tissue thickness and compliance. The graph shows injection depth into various post mortem skin samples as a function of increasing jet velocity. The area of each circle represents the total desired injection volume (20 μL or 100 μL); the percentage quantifies the mean proportion of drug absorbed by the tissue, by weight. Mouse: n=103, CV=0.15@$V_{jet}$ 100 m/s; Guinea pig; n=20, CV=0.31@$V_{jet}$ 100 m/s; Rabbit: n=30, CV=0.03@$V_{jet}$ 100 m/s; n=30, CV=0.02@$V_{jet}$ 200 m/s; Pig: n=20, CV=0.11@$V_{jet}$ 125-150 m/s, n=26, CV=0.08@$V_{jet}$ 150-175 ms/, n=20, CV=0.08@$V_{jet}$ 200 m/s.

In yet another embodiment of servo-controlling based on position (and thereby based on volume delivered), position may be sensed at the piston using a variety of optical or electrical non-contact techniques.

In accordance with the discussion above, a method for injecting a substance through a surface of a biological body includes providing a needle-free transdermal transport device configured to inject the substance through the surface of the biological body. Suitable devices are illustrated in FIGS. 1 and 4; one of skill in the art will recognize that other needle-free injectors may be used with the methods described herein. The substance is injected into the biological body with the transport device while (i) sensing a parameter of the injection; and (ii) a servo-controller is used to dynamically adjust at least one injection characteristic based on the sensed parameter. The sensed parameter may be at least one of position, deformation of an ampoule disposed on the needle-free transdermal transport device, temperature of ambient, temperature of injected substance, sound of substance impinging on the biological body, and/or barometric pressure. The sensed parameter may further include, e.g., injection pressure, sensed pressure within the transport device, position, force, current, and/or voltage. The injection characteristic that is dynamically adjusted is, e.g., depth of injection and volume of injected substance. The substance is injected for (i) a first time period during which a first portion of a volume of the substance is injected at a first injection pressure, and (ii) a second time period during which a remainder of the volume of the substance is injected at a second injection pressure. Prior to injection, the transport device may be pre-programmed with a jet velocity waveform. As discussed above, the jet velocity waveform may include a first jet velocity, a first time period, a second follow-through velocity, and the volume. The second time period may be determined by the needle-free transdermal transport device.

The needle-free transdermal transport device may include a coil, and the injection characteristic may be dynamically controlled on the basis of measured coil displacement. The needle-free transdermal transport device may also include a position sensor, and coil displacement may be measured by sensing the coil displacement with the position sensor.

In some embodiments of the invention, the injection profile may be varied, depending on the structure of the formulation being injected. For example, the injection pressure or jet velocity may be increased when a formulation having a high molecular weight is being administered. The viscosity of a sample may change with a change in, for example the concentration, temperature, or pH, of the biologic or biotherapeutic, and/or the composition of the formulation. In addition, the viscosity of a liquid may also change in response to extremes in pressure and increased shear rate; in the latter case, non-Newtonian fluids such as pseudoplastics (e.g., polymers) experience shear thinning. Accordingly, injection parameters may be varied based on these parameters.

A needle-free transdermal transport device configured to inject the substance through the surface of a biological body, as discussed above, may be provided. A viscosity of the substance to be injected may be pre-programmed into the transport device system. In some embodiments, the viscosity of the substance may be determined indirectly by measuring the force required to fill the ampoule with substance prior to injection; the requisite pressure (or velocity) for delivery being computed from the force assuming fully developed laminar flow.

In yet other embodiments, the viscosity may be sensed during the injection of the substance, a change in the pressure (or velocity) required for delivery being indicative of a change in the viscosity;

$$P = \tfrac{1}{2}\rho v^2 + P\mu \qquad (5)$$

In some other embodiments, the needle-free transdermal transport device may include a servo-controller, and the servo-controller may calculate the injection pressure based on the determined viscosity.

The power consumed for each injection may also provide a useful parameter for inferring a change in viscosity.

Finally, temperature may be used to servo-control the viscosity. The viscosity of a substance may be altered by temperature. At higher jet velocity, shear thinning of a viscous substance may impact the pressure (or velocity) required for delivery. However, at the lower follow-through velocities, change in viscosity may be dominated by temperature with fluctuations in temperature resulting in a change in the viscosity of the substance as determined by the pressure (or velocity) required for delivery in the follow-through phase of the injection.

Reproducible delivery of viscous substances using the servo-controlled jet injector has been demonstrated. For example, referring to FIGS. 10A, 10B, and 10C, graphs depict the relationship between glycerol concentration and viscosity as measured at shear rates ranging from $10^{-3}$ s$^{-1}$ to $10^3$ s$^{-1}$ using a 60 mm diameter 2° cone and plate measuring system at 25° C. (A) and the repeatability of delivery of a user defined volume of glycerol concentrations ranging from 1% through 90% at increasing jet velocities (10B and 10C).

Figure 10B:
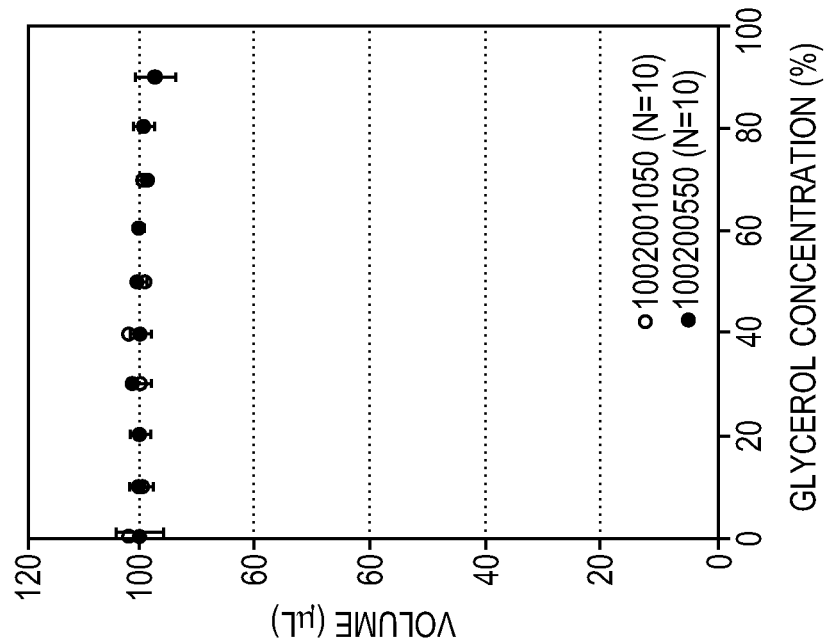
FIGS. 10A, 10B, and 10C are graphs illustrating the determined viscosity of solutions of increasing glycerol concentration, and delivery and repeatability of the volume delivered at each concentration with increasing jet velocities, in accordance with an embodiment of the invention.
Figure 10A:
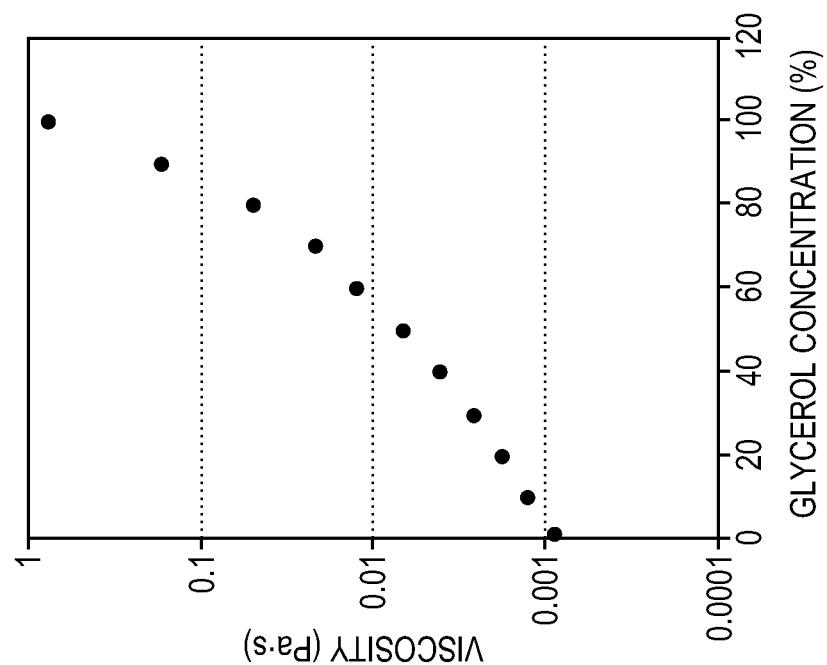
Figure 10C:
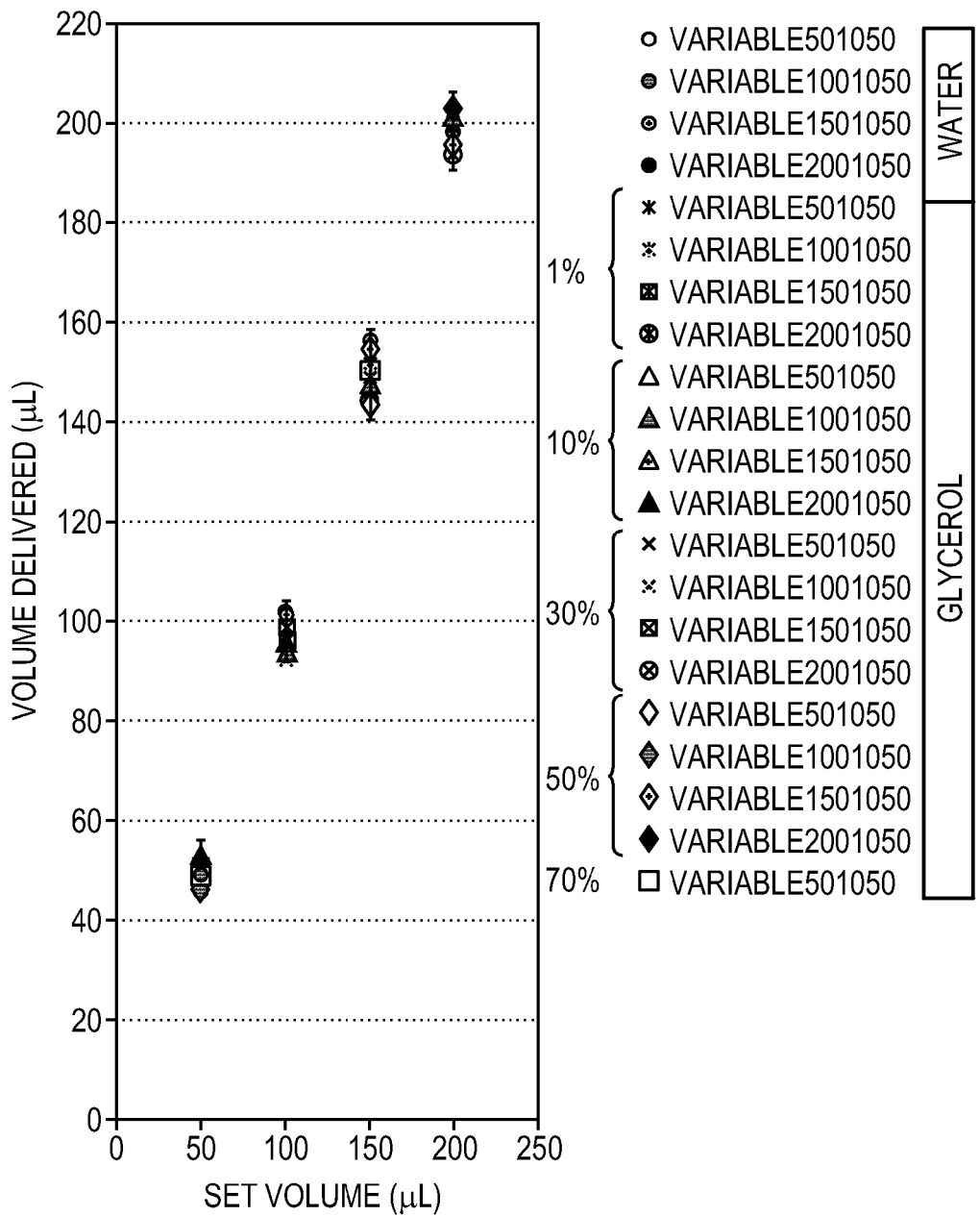

Using the servo-controlled needle-free injector of FIG. 4, with a maximum force output of 200 N, samples having viscosities of ≤0.02 Pa·s (~70%) may be reliably loaded and ejected; the coefficient of variation for volume delivered ranging from an average value of 0.0161 for 0% glycerol to an average value of 0.0119 for 70% glycerol as shown in FIG. 10B. Increasing the force output of the device may result in the ability to deliver samples having viscosities higher than 0.02 Pa·s.

Figure 11B:
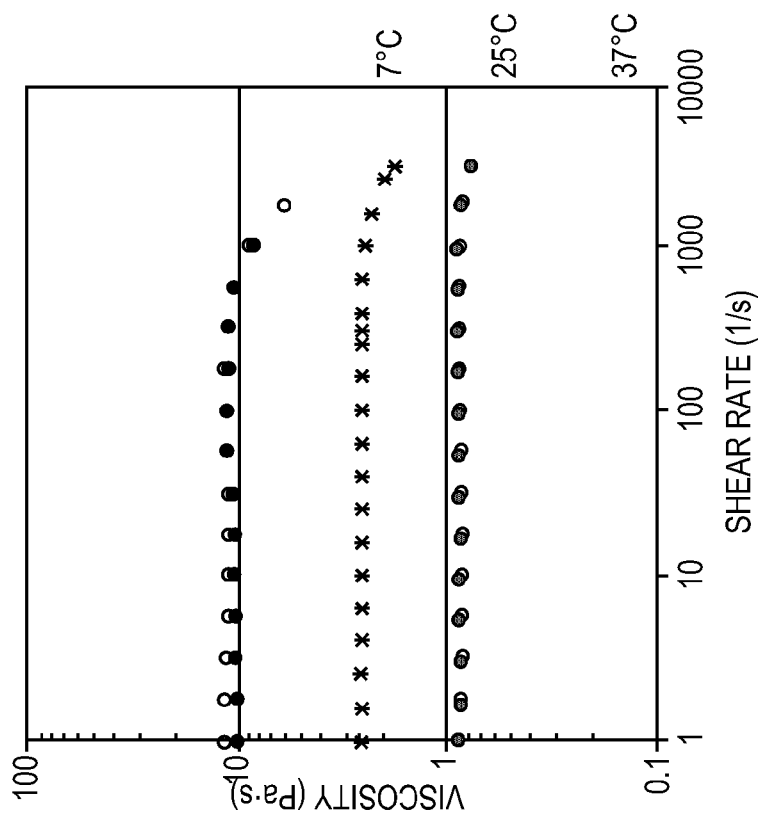
FIGS. 11A and 11B are graphs depicting the viscosity of a polymer as a function of increasing shear rate and a change in viscosity in response to changes in temperature.
Figure 11A:
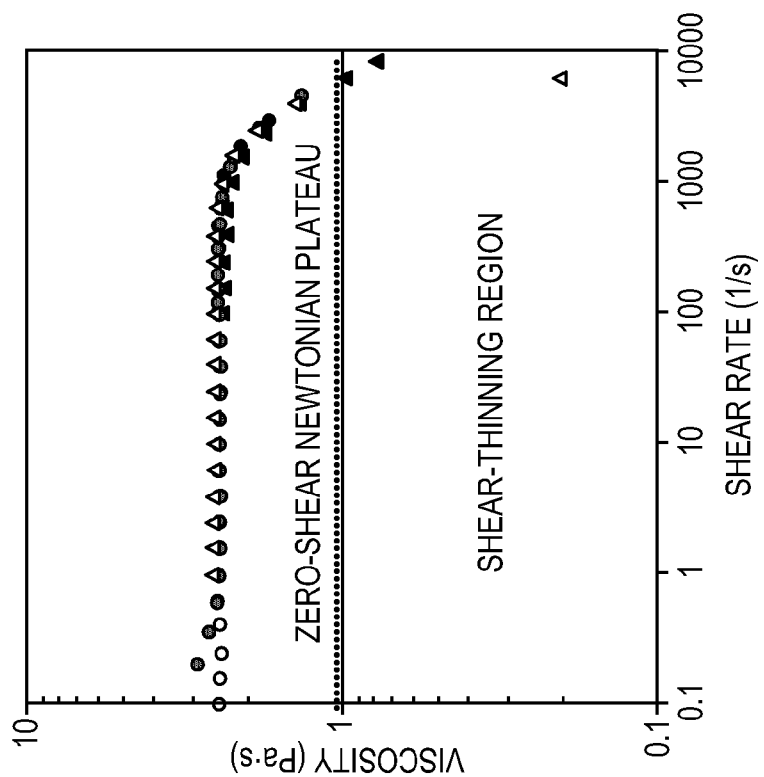

Referring to FIGS. 11A and 11B, graphs depict the behavior of a polymer with increasing shear rate and in response to changes in temperature, respectively. The latter effect may be used to assist delivery of such substances using the servo-controlled jet injector.

The polymer to be delivered may, in some embodiments, be a biological or synthetic polymer that is biodegradable (e.g., collagen, chitosan, polylactic acid, polyorthoester, etc.), thereby enabling controlled release of a drug contained within or embedded in the polymeric structure.

One of skill in the art will recognize that a number of needle-free injectors, in addition to the exemplary needle-free transdermal transport device 100 and hand-held injector 400, may be used in methods in accordance with embodiments of the invention. Moreover, those skilled in the art will readily appreciate that all parameters listed herein are meant to be exemplary and actual parameters depend upon the specific application for which the methods and materials of the present invention are used. It is, therefore, to be understood that the foregoing embodiments are presented by way of example only and that, within the scope of the appended claims and equivalents thereto, the invention may be practiced otherwise than as specifically described. Various materials, geometries, sizes, and interrelationships of elements may be practiced in various combinations and permutations, and all such variants and equivalents are to be considered part of the invention.

What is claimed is:

1. A method for injecting a substance through a surface of a biological body, the method comprising the steps of:
   providing a needle-free transdermal transport device configured to inject the substance through the surface of the biological body; and
   injecting the substance into the biological body with the transport device while
      (i) sensing a parameter associated with the injection, the parameter comprising at least one of deformation of an ampoule disposed on the needle-free transdermal transport device and sound of substance impinging on the biological body; and
      (ii) using a servo-controller to dynamically adjust at least one injection characteristic based on the sensed parameter,
   wherein the substance is injected for (i) a first time period during which a first portion of a volume of the substance is injected at the first injection pressure, and (ii) a second time period during which a remainder of the volume of the substance is injected at a second injection pressure.

2. The method of claim 1, wherein sensing the parameter further comprises sensing at least one of injection pressure, sensed pressure within the transport device, position, volume, mechanical impedance, force, current, and voltage.

3. The method of claim 1, wherein the at least one injection characteristic is selected from the group consisting of depth of injection and volume of injected substance.

4. The method of claim 1, further comprising, prior to injecting the substance, pre-programming the transport device with a jet velocity waveform.

5. The method of claim 4, wherein the jet velocity waveform comprises a first jet velocity, the first time period, a second follow-through velocity, and the volume.

6. The method of claim 5, wherein the second time period is determined by the needle-free transdermal transport device.

7. The method of claim 1, wherein the needle-free transdermal transport device comprises a coil, and the injection characteristic is dynamically controlled on the basis of measured coil displacement.

8. The method of claim 7, wherein the needle-free transdermal transport device comprises a position sensor, and coil displacement is measured by sensing the coil displacement with the position sensor.

9. The method of claim 1, wherein the sensed parameter is deformation of an ampoule disposed on the needle-free transdermal transport device.

10. The method of claim 1, wherein the sensed parameter is sound of substance impinging on the biological body.

11. A control system for a needle-free transdermal transport device configured to inject a substance through a surface of a biological body, the control system comprising:
- a sensor for sensing a parameter of the injection, the sensor selected from the group consisting of a sensor that senses deformation of an ampoule disposed on the needle-free transdermal transport device and a sensor that senses sound of substance impinging on the biological body; and
- a servo-controller to dynamically adjust at least one injection characteristic based on the sensed parameter,
- wherein the sensor and the servo-controller control the injection of the substance such that the substance is injected for (i) a first time period during which a first portion of a volume of the substance is injected at a first injection pressure, and (ii) a second time period during which a remainder of the volume of the substance is injected at a second injection pressure.

12. The control system of claim 11, wherein the sensor is a sensor that senses deformation of an ampoule disposed on the needle-free transdermal transport device.

13. The control system of claim 11, wherein the sensor is a sensor that senses sound of substance impinging on the biological body.

14. The control system of claim 12, wherein the sensor is a strain gauge.

15. The control system of claim 13, wherein the sensor is an acoustic sensor or transducer.

* * * * *